US00PP13685P39

(12) United States Plant Patent
Delbard

(10) Patent No.: US PP13,685 P3
(45) Date of Patent: Mar. 25, 2003

(54) HYBRID TEA ROSE PLANT NAMED 'DELBIROS'

(75) Inventor: Arnaud Delbard, Malicorne (FR)

(73) Assignee: Societé Anonyme des Pépiniéres et Roseraies Georges Delbard, Commentry (FR)

( * ) Notice: Subject to any disclaimer, the term of this patent is extended or adjusted under 35 U.S.C. 154(b) by 0 days.

(21) Appl. No.: 09/830,000

(22) Filed: Apr. 11, 2001

(65) Prior Publication Data

US 2002/0078480 P1 Jun. 20, 2002

(30) Foreign Application Priority Data

Dec. 20, 2000 (FR) ..... 17531

(51) Int. Cl.[7] ..... A01H 5/00
(52) U.S. Cl. ..... Plt./132
(58) Field of Search ..... Plt./132

(56) References Cited

PUBLICATIONS

UPOV–ROM GTITM Computer Database, 2001/06, GTI Retrieval Software, citation for 'Delbiros'.*

* cited by examiner

*Primary Examiner*—Bruce R. Campell
*Assistant Examiner*—Susan B. McCormick
(74) *Attorney, Agent, or Firm*—Burns, Doane, Swecker & Mathis, LLP

(57) ABSTRACT

A new and distinct variety of Hybrid Tea rose plant is provided that abundantly and nearly continuously forms attractive bicolored double flowers which are light pink and darker pink. The plant is well suited for cut flower production when grown in the greenhouse. The flowers exhibit a good vase life and possess petals that detach cleanly. The plant exhibits a bushy growth habit, forms semi-vigorous to vigorous medium glossy vegetation, and is well suited for forcing when producing cut flowers. Additionally, the plant displays good disease resistance.

1 Drawing Sheet

BOTANICAL/COMMERCIAL CLASSIFICATION

Figures 1, 2, 3, 4, 5, 6, 7, 8, 9, 10, 12, 13, 14, 15, 16:
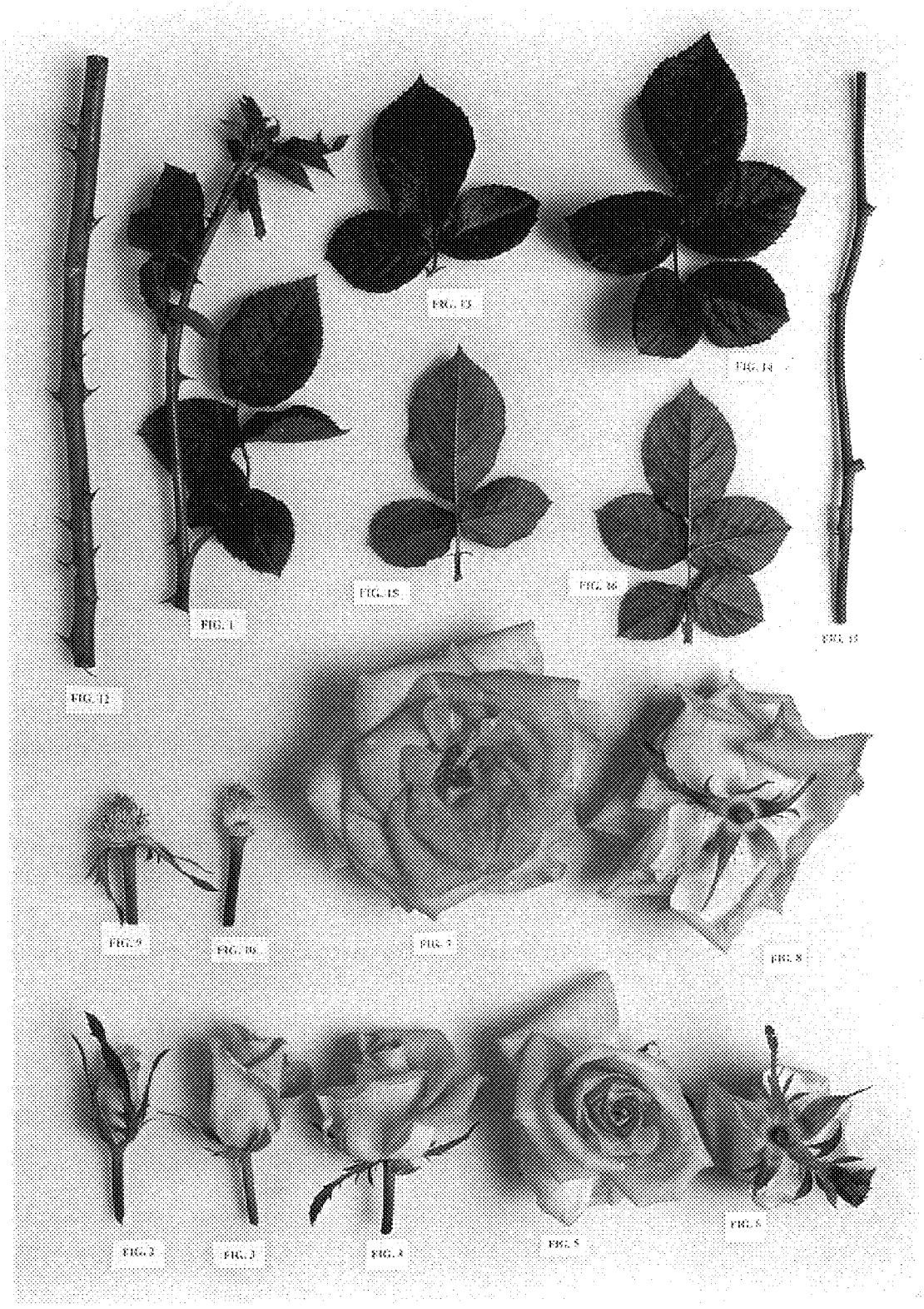

*Rosa hybrida*/Hybrid Tea Rose Plant.

VARIETAL DENOMINATION cv. 'Delbiros'.

SUMMARY OF THE INVENTION

The new variety of *Rosa hybrida* Hybrid Tea rose plant was created in France by artificial pollination wherein two parents were crossed which previously had been studied in the hope that they would contribute the desired characteristics. The female parent (i.e., the seed parent) was the 'Krimony' variety (U.S. Plant Pat. No. 8,845). The male parent (i.e., the pollen parent) was the 'Meicofum' variety (U.S. Plant Pat. No. 9,997). The parentage of the new variety can be summarized as follows:

'Krimony'×'Meicofum'.

The seeds resulting from the above pollination were sown and 189 small plants were obtained that were physically and biologically different from each other. Selective study resulted in the identification of a single plant of the new variety.

It was found through careful study that the new variety of Hybrid Tea rose plant of the present invention exhibits the following combination of characteristics:

(a) from a physical point of view forms green mature wood, displays a bushy growth habit, and forms attractive long-lasting bicolored light pink and darker pink double flowers, and (b) from the biological point of view forms semi-vigorous to vigorous vegetation, produces flowers in abundance, exhibits the ability readily to be forced, and is resistant to diseases.

The new variety well meets the needs of the horticultural industry and is particularly well suited for growing in the greenhouse for the production of attractive long-lasting turbinate cut flowers which are a bicolored clear light pink and darker pink.

The new variety can be readily distinguished from its parental varieties in view of the combination of characteristics described herein. For instance, the 'Krimony' variety commonly forms flowers having approximately 45 petals while those of the new variety commonly display approximately 32 petals. Also, the 'Krimony' variety forms broad-ovate flower buds while the flower buds of the new variety are ovate. The flowers of the 'Meicofum' variety are darker in coloration than those of the new variety, and the buds of the 'Meicofum' variety prior to the break of the calyx are shorter and commonly measure approximately 25 mm in length while those of the new variety commonly measure approximately 29 mm in length.

The new variety exhibits medium length and relatively straight stems, rigid and substantially straight peduncles, an excellent ability to be forced under greenhouse growing conditions, and a good vase life for the distinctive clear pink and darker pink turbinate blossoms.

The new variety has been found to undergo asexual propagation and can be readily reproduced by conventional routes, such as budding (i.e., eye grafting), the rooting of cuttings and tissue culture. Asexual reproduction by the above-identified routes as performed at Hyéres, France, has demonstrated that the characteristics of the new variety are stable and are strictly transmissible from one generation to another.

The new variety has been named the 'Delbiros' variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass in the South of France.

FIG. 1—illustrates a specimen of a young shoot;

FIG. 2—illustrates a specimen of a floral bud at the opening of the sepals;

FIG. 3—illustrates a specimen of a floral bud at the opening of the petals;

FIG. 4—illustrates a specimen of a flower in the course of opening;

FIG. 5—illustrates a specimen of an open flower—plan view—obverse;

FIG. 6—illustrates a specimen of an open flower plan view—reverse;

FIG. 7—illustrates a specimen of a fully open flower plan view—obverse;

FIG. 8—illustrates a specimen of a fully open flower plan view—reverse;

FIG. 9—illustrates a specimen of a floral receptacle showing the arrangement of the stamens and pistils;

FIG. 10—illustrates a specimen of a floral receptacle showing the arrangement of the pistils (stamens and sepals removed);

FIG. 11—illustrates a specimen of a flowering stem;

FIG. 12—illustrates a specimen of a main branch (upside down);

FIG. 13—illustrates a specimen of a leaf with three leaflets—plan view—upper surface;

FIG. 14—illustrates a specimen of a leaf with five leaflets—plan view—upper surface;

FIG. 15—illustrates a specimen of a leaf with three leaflets—plan view—under surface; and FIG. 16—illustrates a specimen of a leaf with five leaflets—plan view—under surface.

DETAILED DESCRIPTION

The chart used in the identification of the colors is that of The Royal Horticultural Society (R.H.S. Colour Chart), London, England. The description is based on the observation of plants grown under glass in the South of France. The coloration in common terms sometimes also is provided.

Class: Hybrid Tea.

Plant:

*Height.*—Plants which were pruned to a height of 20 to 30 cm produce floral stems having a length of approximately 40 to 100 cm, and an average length of approximately 70 cm.

*Width.*—Approximately 50 to 60 cm.

*Habit.*—Bushy.

Branches:

*Color.*—Young shoots: when approximately 30 cm long, exhibit a greenish-red coloration, Yellow-Green Group 152A to Greyed-Red Group 178A. Floral stems: Yellow-Green Group 144A to 146B in coloration, and approximately 5 to 10 mm (average approximately 7 mm) in diameter. Mature wood: Yellow-Green Group 144B in coloration with pigments of Green Group 143C, and approximately 9 to 15 mm (average 12 mm) in diameter.

*Thorns.*—Configuration: convex on the upper edge and concave on the under edge. Quantity, length and frequency: on a typical floral stem having a length of 50 cm, there commonly are no thorns on the approximately 25 cm below the bud, and for the next approximately 25 cm some thorns are irregularly arranged having lengths of approximately 3 mm to 1 cm and an average length of approximately 76 mm. On a young shoot having a length of approximately 25 cm, there commonly are no thorns. Color: on floral stems the coloration of the thorns is Green Group 143C, and on mature wood the thorns are Greyed-Orange Group 165A and 165B.

*Leaves.*—Number: typical for the class, and commonly approximately 80 to 100 per plant. Size: medium, and commonly the leaves measure in length approximately 14 to 20 cm (average approximately 17 cm), and in width approximately 9 to 16 cm (average approximately 13 cm). Stipules: adnate, typical for the class, approximately 18 to 20 cm (average approximately 19 cm) in length, approximately 7 to 9 mm (average approximately 8 mm) in width at the mid-point, approximately 10 to 14 mm (average approximately 12 mm) in width at the distal end, Yellow-Green Group 143B on the upper surface, and Yellow-Green Group 143C on the under surface.

*Leaflets.*—Number: 3, 5, and 7. Size: very large. Shape: rounded to cordate at the base of the terminal leaflet and convex in cross section. Serration: present, single, and irregular. Venation: alternate pattern, near Yellow-Green Group 151B at the distal end, and near Greyed-Yellow Group 160A at the proximal end. General appearance: consistent with medium glossiness. Petiole: the inner surface is grooved with non-glandular edges, and commonly 1 to 6 prickles are present per petiole. Petiole color on young shoot: on the upper surface bronze, Greyed-Orange Group 173A, and green at the base, and similar in coloration on the under surface. Petiole color on floral stem: on the upper surface bronze, Greyed-Orange Group 176A and Yellow-Green Group 152C at the base, and Yellow Green Group 152B on the under surface. Petiole color on mature wood: on the upper surface Yellow-Green Group 144B and Yellow-Green Group 144B on the under surface. Petiole length of terminal leaflet: approximately 9 to 15 mm, approximately 12 mm on average, with a standard deviation of 0.20 mm. Terminal leaflet length: approximately 70 to 80 mm, approximately 75 mm on average, with a standard deviation of 0.38 mm. Terminal leaflet width: approximately 42 to 60 mm, approximately 48 mm on average, with a standard deviation of 0.54 mm. Terminal leaflet shape at base: rounded. Leaflet color of young shoot: Yellow-Green Group 146A with some bronze coloration on the upper surface and Yellow-Green Group 148B on the middle of the under surface. Leaflet color on floral stem: Yellow-Green Group 147A on the upper surface and Yellow-Green Group 147B on the under surface. Leaflet color of mature wood: Yellow-Green Group 146A on the upper surface, and Yellow-Green Group 147B on the under surface.

Inflorescence:

*Number of flowers.*—Generally one per stem when grown under forced greenhouse conditions;

however, sometimes during forced culture an axillary eye or eyes below the flower develop to form 1 or 2 flowers.

*Peduncle.*—Erect, stiff, Yellow-Green Group 144A in coloration with some small hairs, approximately 50 to 60 mm (average 55 mm) in diameter, and approximately 80 to 160 mm in length.

*Sepals.*—Configuration: Two sepals commonly possess no extensions, and three sepals commonly possess medium to strong extensions. The extensions are classified medium to strong in accordance with UPOV Guideline TG/11/7 (October 1990) for roses. Length: approximately 40 mm on average. Color: Yellow-Green Group 147C on the upper surface and Yellow-Green Group 146C on the under surface.

*Buds.*—Shape: ovate in longitudinal section just before the opening of the sepals. Size before calyx breaks: the bud lengths commonly are approximately 28 to 30 mm, with an average length of approximately 29 mm, and the bud diameters commonly are approximately 15 to 20 mm. Color as calyx breaks: Yellow Group 2D to Yellow Group 6C. Size after calyx breaks: as first petals of the second row open, the bud lengths are approximately 31 to 50 mm, with an average length of approximately 47 mm. Color after calyx breaks: as first petals of the second row open, on the inside Orange-Red Group 33C at the margin and Orange-Red Group 32C at the central zone.

*Flower.*—Time: medium flowering (i.e, when grown under glass at a temperature of 16 to 25° C. the variety commonly blooms approximately 50 days in the spring). Shape: double. Form: irregularly rounded when viewed from above, flattened convex at the upper part when viewed from the side, and flattened convex to convex at the lower part when viewed from the side. Diameter: medium to large, approximately 10 to 12 cm, and approximately 11 cm on average, with a standard deviation of 0.5 cm. Petal number: commonly approximately 30 to 34, and an average of approximately 32. Petal size (second row from outside): the length is approximately 63 to 70 mm with a mean of approximately 65 mm, and a standard deviation of 0.27 mm; and the width is approximately 60 to 66 mm with a mean of approximately 63 mm, and a standard deviation of 2.8 mm. Petal shape: the first row of petals commonly exhibits a broad ovate configuration, the undulation of the petal margins is average, and the reflexing of the margins when flowers are open is average. Petal color: the following description of a nearly fully open flower was made while observing a rose grown in the greenhouse during October which had been undergoing opening for three days. Petal color (middle zone): on the inner surface White Group 155D suffused with Red Group 49A, and on the outer surface White Group 155C. Petal color (marginal zone): on the inner surface White Group 155D suffused with Red Group 49A, and on the outer surface White Group 155C. Petal spot at base: large in size. Color of spot inner side: Yellow Group 12B. Color of spot outer side: pale yellow, Yellow Group 10A with a margin of Yellow Group 2D. Stamens: approximately 80 in number and are somewhat regularly arranged below the level of the pistils. Filaments: medium in length, not all possess an anther, when the flower is partially open Orange Group 24A in coloration, and when the flower is fully open Yellow-Orange Group 23A in coloration. Anthers: medium in size, all open at approximately the same time, and the immature coloration is Yellow-Orange Group 14B. Pollen: sparse in quantity and Yellow-Orange Group 21A in coloration. Pistils: approximately 100 in number. Styles: medium in length and Yellow-Orange 18D with tips of Red-Purple Group 65A in coloration. Stigmas: Yellow Group 12B. Hips: in longitudinal section they are in the shape of a pitcher and are approximately 16 mm in diameter. Seeds: Green-White Group 157B in coloration and approximately 7 mm in length. Petal drop: the petals detach cleanly. Fragrance: medium and sweet. Lasting quality: long. When cut and placed in a vase, the flowers commonly last approximately 10 to 11 days on average.

Development:

*Vegetation.*—Semi-vigorous to vigorous. Commonly approximately 45 to 70 cm of new growth forms over a two-month period of time.

*Blooming.*—Very abundant and almost continuous.

*Propensity to root.*—Approximately 20 to 25 days commonly are required to initiate rooting.

*Aptitude to forcing.*—Excellent.

*Hardiness.*—To date the new variety has been grown exclusively under glass. Accordingly, the hardiness of the variety when grown outdoors has not been evaluated.

*Resistance to diseases.*—Good under greenhouse conditions, as well as when grown outdoors.

*Resistance to drought/heat.*—Typical of the species during observations to date.

I claim:

1. A new and distinct variety of Hybrid Tea rose plant characterized by the following combination of characteristics:

(a) from a physical point of view forms green mature wood, displays a bushy growth habit, and forms attractive long-lasting bicolored light pink and darker pink double flowers, and (b) from the biological point of view forms semi-vigorous to vigorous vegetation, produces flowers in abundance, exhibits the ability readily to be forced, and is resistant to diseases;

substantially as herein shown and described.

* * * * *